US010052458B2

United States Patent
Fischer et al.

(10) Patent No.: US 10,052,458 B2
(45) Date of Patent: Aug. 21, 2018

(54) SYSTEM AND METHOD FOR UNDERACTUATED CONTROL OF INSERTION PATH FOR ASYMMETRIC TIP NEEDLES

(71) Applicant: WORCESTER POLYTECHNIC INSTITUTE, Worcester, MA (US)

(72) Inventors: Gregory S. Fischer, Boston, MA (US); Hao Su, Somerville, MA (US)

(73) Assignee: WORCESTER POLYTECHNIC INSTITUTE, Worcester, MA (US)

( * ) Notice: Subject to any disclaimer, the term of this patent is extended or adjusted under 35 U.S.C. 154(b) by 149 days.

(21) Appl. No.: 14/056,205

(22) Filed: Oct. 17, 2013

(65) Prior Publication Data

US 2014/0107569 A1     Apr. 17, 2014

Related U.S. Application Data

(60) Provisional application No. 61/715,063, filed on Oct. 17, 2012.

(51) Int. Cl.
    *A61M 5/32*     (2006.01)
    *A61B 34/30*     (2016.01)
    (Continued)

(52) U.S. Cl.
    CPC ......... *A61M 25/0152* (2013.01); *A61B 34/30* (2016.02); *A61B 34/37* (2016.02);
    (Continued)

(58) Field of Classification Search
    CPC .. A61M 5/3287; A61M 5/46; A61M 25/0152; A61M 2005/3289;
    (Continued)

(56) References Cited

U.S. PATENT DOCUMENTS

| | | | |
|---|---|---|---|
| 5,345,937 A | | 9/1994 | Middleman et al. |
| 5,938,635 A | * | 8/1999 | Kuhle ................. A61M 5/3286 604/272 |

(Continued)

FOREIGN PATENT DOCUMENTS

| | | |
|---|---|---|
| WO | 2009097539 A2 | 8/2009 |
| WO | 20090152613 A1 | 12/2009 |
| WO | 2012095845 A1 | 7/2012 |

OTHER PUBLICATIONS

Wood, et al., Needle Steering System using Duty-Cycled Rotation for Percutaneous Kidney Access, 32nd Annual International Conference of the IEEE EMBS, Aug. 31-Sep. 4, 2010, Buenos Aires, Argentina.

(Continued)

*Primary Examiner* — Stephen Holwerda
(74) *Attorney, Agent, or Firm* — Michael G. Johnston; Moore & Van Allen PLLC

(57) ABSTRACT

A needle steering system and apparatus provides active, semi-autonomous control of needle insertion paths while still enabling a clinician ultimate control over needle insertion. The present teaching describes a method and system for controlling needle path as the needle is inserted by precisely controlling the rotation of the needle as it continuously rotates during insertion. This enables underactuated 2 degree-of-freedom (DOF) control of the direction and the curvature of the needle from a single rotary actuator. Control of the rotary motion is therefore decoupled from the needle insertion. The rotary motion controls steering effort and direction, while the insertion controls needle depth or insertion speed. In one implementation, the proposed method does not require constant velocity insertion, interleaved insertion and rotation, or known insertion position or speed. The insertion may be provided by a robot or other automated (Continued)

method, may be a manual insertion, or may be a teleoperated insertion.

8 Claims, 18 Drawing Sheets

(51) Int. Cl.
A61M 25/01 (2006.01)
A61M 5/46 (2006.01)
A61B 34/37 (2016.01)
A61B 34/00 (2016.01)

(52) U.S. Cl.
CPC ............ *A61M 5/3287* (2013.01); *A61M 5/46* (2013.01); *A61B 34/76* (2016.02); *A61B 2034/301* (2016.02); *A61B 2034/302* (2016.02); *A61M 25/0116* (2013.01); *A61M 2005/3289* (2013.01); *A61M 2205/50* (2013.01)

(58) Field of Classification Search
CPC ........... A61M 2205/50; A61M 25/0116; A61B 19/2203; A61B 2019/2211; A61B 2019/2223; A61B 2019/2292; B25J 9/10; B25J 9/1015; B25J 9/102; B25J 9/1075; B25J 9/12; B25J 9/126; B25J 9/146
USPC .......................................... 604/95.01, 93.01
See application file for complete search history.

(56) References Cited

U.S. PATENT DOCUMENTS

| | | | |
|---|---|---|---|
| 6,398,755 B1* | 6/2002 | Belef | A61B 8/12 604/95.01 |
| 7,822,458 B2 | 10/2010 | Webster, III | |
| 8,348,861 B2 | 1/2013 | Glozman et al. | |
| 2004/0133168 A1 | 7/2004 | Salcudean et al. | |
| 2007/0016067 A1* | 1/2007 | Webster, III | A61B 17/3403 600/464 |
| 2008/0009791 A1* | 1/2008 | Cohen | A61M 25/0105 604/95.01 |
| 2009/0138025 A1* | 5/2009 | Stahler | A61B 34/71 606/130 |
| 2009/0149867 A1 | 6/2009 | Glozman | |
| 2010/0217117 A1* | 8/2010 | Glossop | A61B 8/4245 600/424 |
| 2011/0112549 A1 | 5/2011 | Neubach et al. | |
| 2013/0109919 A1* | 5/2013 | Sugiyama | A61B 1/0052 600/117 |
| 2013/0204124 A1 | 8/2013 | Duindam et al. | |
| 2013/0225996 A1 | 8/2013 | Dillard et al. | |
| 2014/0107569 A1* | 4/2014 | Fischer | A61M 5/3287 604/95.01 |

OTHER PUBLICATIONS

Webster, et al. Nonholonomic Modeling of Needle Steering, Int'l. Journal of Robotics Research, May-Jun. 2006, pp. 509-525, vol. 25, No. 5-6, SAGE Publications.
Worcester Polytechnic Institute, et al., European Application No. 13846488.8, Extended European Search Report, dated Jun. 1, 2016.

* cited by examiner

SYSTEM AND METHOD FOR UNDERACTUATED CONTROL OF INSERTION PATH FOR ASYMMETRIC TIP NEEDLES

CROSS REFERENCE TO RELATED APPLICATIONS

This application claims the benefit of the filing date of earlier filed U.S. Provisional Application Ser. No. 61/715,063, filed Oct. 17, 2012, entitled "SYSTEM AND METHOD FOR UNDERACTUATED CONTROL OF INSERTION PATH FOR ASYMMETRIC TIP NEEDLES" the teachings, disclosures and contents of which are incorporated herein by reference in entirety.

FIELD OF INVENTION

The disclosed configuration relates to a system and approach for controlling insertion paths of needles with asymmetric tips for therapeutic and diagnostic medical interventions, and especially underactuated control of needle curvature and direction decoupled from needle insertion.

BACKGROUND

Needle-based interventions are commonplace. These may be used for a variety of percutaneous diagnostic and therapeutic interventions. However, ensuring that the needle, cannula, or other instrument makes it to the desired target while following a desired path is often nontrivial. Inaccuracy may come from various causes including needle deflection, tissue deformation, target motion, patient motion, or other sources. Many needles have asymmetric tip shapes, such as a beveled tip and/or cannula. In some cases, these tips cause asymmetric forces on the needle that cause it to deflect as it is inserted. This deflection in many cases is undesirable and results in errors in needle placement. However, some clinicians use the asymmetric tip forces to their advantage and actively control or steer the needle path during insertion by rotating the bevel direction. Further, others have attempted continuous rotation or drilling of a needle to ensure that it follows a straight insertion path.

SUMMARY

The present disclosure teaches active, semi-autonomous control of needle insertion paths while still enabling a clinician ultimate control over needle insertion. The present teaching describes a method and system for controlling needle path as the needle is inserted by precisely controlling the rotation of the needle as it continuously rotates during insertion. This enables underactuated 2 degree-of-freedom (DOF) control of the direction and the curvature of the needle from a single rotary actuator. An advantage of the disclosed configuration is that control of the rotary motion may be decoupled from the needle insertion. The rotary motion controls steering effort and direction, while the insertion controls needle depth or insertion speed. In one implementation, the proposed method does not require constant velocity insertion, interleaved insertion and rotation, or known insertion position or speed. The insertion may be provided by a robot or other automated method, may be a manual insertion, or may be a teleoperated insertion.

Control of the needle path may be used in multiple cases. In one case, as the needle is inserted an error is determined between the projection of the needle and the target, so a compensation in the needle path is required. In other cases, a specific path or trajectory is desired, and the needle is controlled along that path to reach the target. In a combined case, a predetermined path is defined, and compensation is required as the needle is inserted to ensure the path is followed and the endpoint reached. These control approaches may be open loop or closed loop. The closed loop approach may be based upon medical imaging or image-guidance such as ultrasound, x-ray, fluoroscopy, computed tomography (CT), magnetic resonance imaging (MRI), video feeds, laser scans, external tracking systems, or other approaches.

The present teaching relates generally to controlling the trajectory of a needle or other instrument with an asymmetric tip. The disclosed arrangement describes a method for underactuated control of needle direction and curvature as it is inserted into tissue that is decoupled from the needle insertion motion. The approach also describes a system and components for implementing the proposed method.

In a particular configuration, the disclosed approach employs a method for inserting a needle with a asymmetric shaped tip into tissue along a curved path, wherein the needle is continuously rotated at a time-varying angular velocity; wherein the time-varying angular velocity rotation is a function of the needle angular position.

An example needle steering apparatus suitable for use with configurations herein includes a needle having an asymmetric tip, the asymmetric tip defined by a beveled cut across a cylindrical cross section of the needle, and a rotary drive for rotating the needle along a needle axis. The rotary drive is responsive to control logic adapted to rotate the needle at an angular velocity based on an angular position, and invokes an inserter for disposing the needle axially in a direction of an axis of rotation, such that the angular velocity is independent from the insertion.

In operation, in a surgical environment having an asymmetric tipped needle and a needle driving apparatus responsive to rotational and insertion control, the method of directing the needle includes identifying a steering trajectory path for the needle, and controlling a time-varying rotation speed of the needle based on the identified steering path, such that the rotation speed determines a relative duration that a bevel angle of the needle applies force in a direction corresponding to the steering trajectory. The rotation is decoupled from advancement of the needle resulting from control of the controlled rotation speed about the needle axis, such that the controlled rotation speed is based on an angle of rotation, and independent of the linear advancement of the needle from the insertion control, so that the needle follows the prescribed path regardless of the insertion speed.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
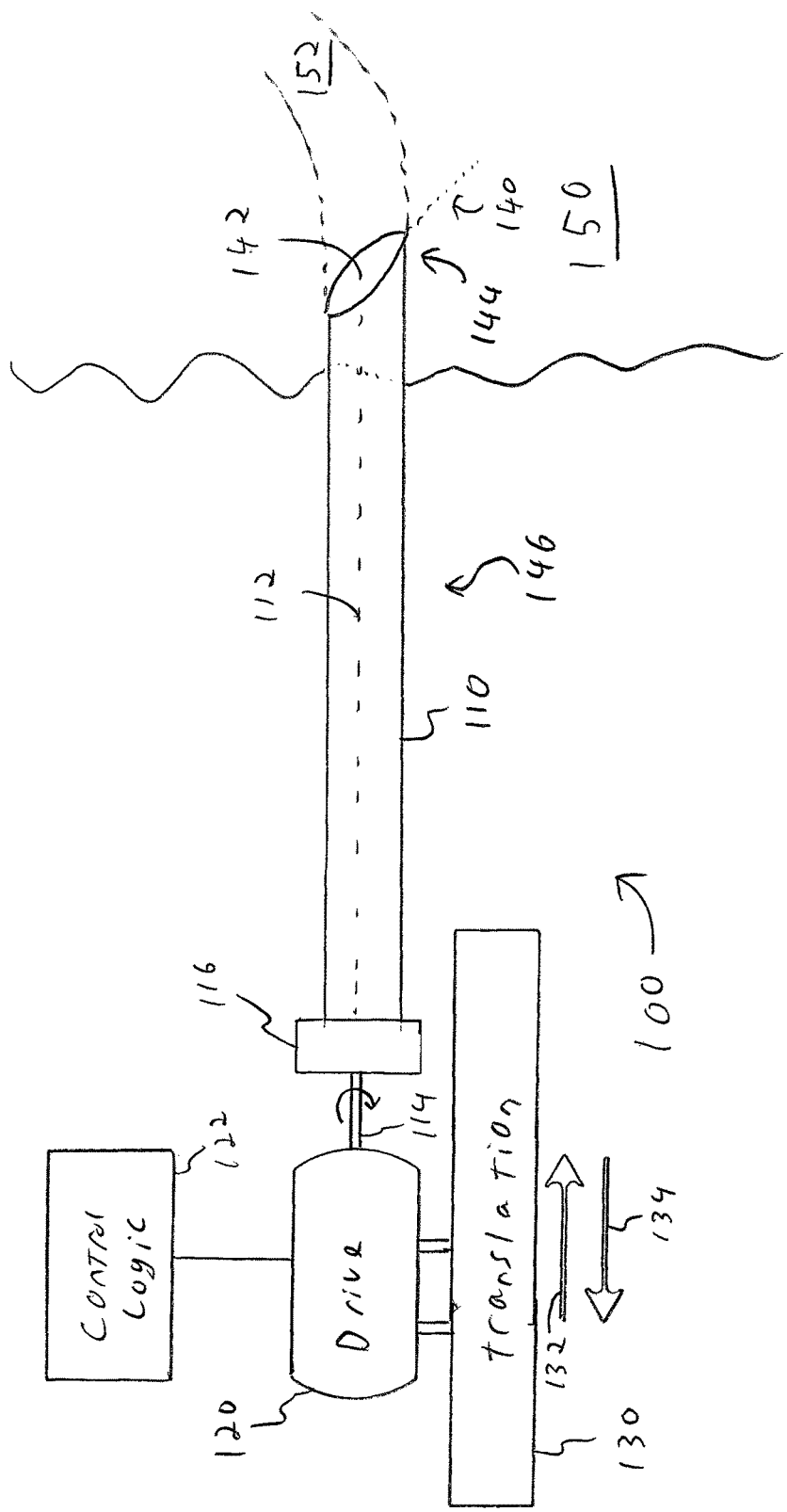
FIG. 1 shows a context diagram of major components of the steerable needle assembly and mechanism suitable for use with configurations herein.

Configurations disclosed below teach a mechanism referred to as the Continuous Uncoupled Rotation Velocity-independent (CURV) steering approach. The described approach is one example, however the disclosed configuration also includes other related variants of decoupled, underactuated control of needle insertion based on asymmetric tips. The disclosed configuration also describes a plethora of systems and components for implementing the proposed approach. In one embodiment, a robotic needle driver provides 2 DOF control of needle rotation and insertion, thus providing 3 DOF control of the tip (i.e. can place the tip to a 3D position using 2 actuators). The needle driver may further be configured as part of a robotic system. The system may further be configured to incorporate a teleoperation master that a user manipulates to control needle insertion and/or steering angle. The configuration may further include force sensing and haptic feedback. The haptic feedback may be related to the forces on the needle, errors determined by a control system, external factors, or some combination of factors. In one configuration, a user manipulates the teleoperation master along only the insertion axis to control the insertion depth, while the robot automatically steers the needle path according to the disclosed configuration. This may be used based on preoperative path planning, or actively and semi-autonomously compensating for errors as the needle is inserted. In a further embodiment, the rotation is manipulated according to the disclosed configuration by an actuator in a standalone device, and in particular configurations the device may be handheld. The device can control steering effort (related to needle curvature in tissue during insertion) and in alternate configurations may also control angle and/or depth relative to the handle. In an additional embodiment of the disclosed approach, the asymmetric tip control methods taught in the disclosed configuration may be coupled with concentric precurved or prebent tubes or cannulas to provide additional dexterity and control during needle insertion.

Additional advantages of the disclosed configuration will become readily apparent to those skilled in this art from the following detailed description, wherein only selected embodiments of the disclosed configuration are shown and described. As will be realized, the disclosed configuration is capable of other and different embodiments, and its several details are capable of modifications in various obvious respects, all without departing from the invention disclosed herein. Accordingly, the drawings and description are to be regarded as illustrative in nature, and not as restrictive.

The present teachings are described more fully hereinafter with reference to the accompanying drawings, in which the present embodiments are shown. The following description is presented for illustrative purposes only and the presented teachings should not be limited to these embodiments.

In this disclosure, the term "needle" is defined as cylindrical instrument that interacts with tissues, including but not limited to medical needles, electrodes, tubes, rods, and cannulae. The term needle axis refers to the axis along the needle, or subsection thereof. The needles can typically be inserted and rotated along and about thus axis, respectively. In some cases torsional affects make the rotation at various points along the needle unequal, and this can be compensated for if necessary to control the desired subsection of the needle, such as the tip form the base. The term asymmetric tip generally refers to a bevel-shaped tip on a needle, however more broadly it is defined as any feature on a needle that provide asymmetric forces that alter the insertion path as it is inserted.

The examples and discussion that follows employ a surgical context as an example implementation, such that the a surgical needle or cannulated instrument adapted for surgical use is a steerable member, and a medium employed for drilling is surgical tissue. Alternate configurations may employ alternate arrangements of a steerable member and a medium. For example, geological applications may employ steering for exploration of geological structures, such as rock and soil. Alternate configurations may also be employed for building materials such as concrete or wood, or other medium responsive to the steering methodology disclosed herein.

Figure 2:
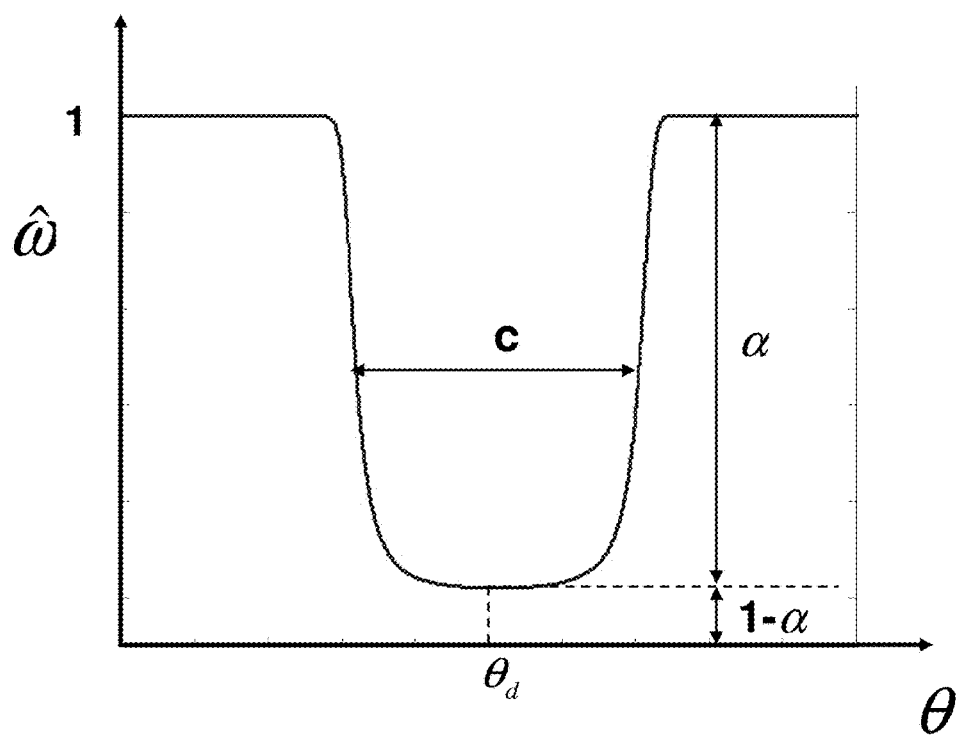
FIG. 2 shows one implementation of the control algorithm for determining needle angular velocity as a function of a current angle.

FIG. 1 shows a context diagram of major components of the steerable needle assembly and mechanism suitable for use with configurations herein. Referring to FIG. 1, in a surgical environment 100, a surgical needle 110 rotates about a needle axis 112 responsive to a drive shaft 114. Surgical needle 110 may be a solid rod, or may be comprised of multiple coaxial elements. A hub 116 or other coupling engages the needle 110 to the hub 116 for engaging a drive source 120, such as an electric or pneumatic motor, for rotating the drive shaft 114. Hub 116 may comprise a disposable, sterilizable collet or other coupling device to couple needle 110 to drive 120. The drive 120 is responsive to control logic 122 for controlling rotation for providing the steering capability, as disclosed further below. An inserter 130 or other source of movement provides linear translation for inserting 132 or withdrawing 134 the needle 110, shown by respective arrows. Control logic 122 may be responsible for controlling rotation drive 120 and translation inserter 130, or it may only control rotation drive 120 independent of inserter 130. Control logic 122 may be incorporated into an external device such as a robot controller that controls one or more DOF of the device. Translation may be provided by any suitable mechanism, such as a linear actuator (hydraulic, pneumatic or electric), threaded engagement, manual insertion, or other suitable force. The needle 110 has a needle insertion control angle 140 defined by a bevel cut across a cross section of the needle 110 or at least one of its components. In other words, in a cannulated needle arrangement, either the inner needle or the outer cannula may be beveled, or both may share a coplanar beveled face 142 for greater steering capability. The bevel cut defines a bevel face 142 at the needle insertion control angle 140 with respect to the needle axis 112, collectively defining an asymmetric tip 144 at the end of the needle frame 146, forming the integral needle 110 structure. Needle frame 146 refers to a coordinate frame fixed to a point at or near the tip of the needle. Insertion of the needle 110 by the inserter 130 into a surgical material 150 or other medium, typically soft tissue, coupled with rotation by the drive 120, causes the bevel face 142 to engage and displace the surgical material 150 or other medium for steering the needle along a desired path 152, as shown by dotted lines. Steering ability is responsive to varying the rotation speed, discussed below, independently of the insertion speed. FIG. 2 shows one implementation of the control algorithm for determining needle angular velocity as a function current angle. Referring to FIG. 2, this approach enables control of steering effort (related to needle path curvature) and the steering direction using only one actuated rotation degree-of-freedom. The approach is decoupled from the needle insertion motion.

In one embodiment of the disclosed configuration, the needle path direction and curvature is controlled using the approach detailed below and shown in FIG. 2. In this approach, the needle is continuously rotated, and the rotation angle of the needle about its primary axis is computed as a function of the current angle and the desired direction.

In one approach, the normalized angular velocity of the needle about its primary axis is defined using the Gaussian distribution as:

$$\hat{\omega}(\theta, \theta_d) = 1 - \alpha e^{-\frac{(\theta - \theta_d)^2}{2c^2}}$$

Where:
  $\hat{\omega}(\theta, \theta_d)$: normalized needle rotation angular velocity about its primary axis
  $\theta$: current needle angle about its primary axis
  $\theta_d$: needle rotation angle corresponding to desired steering direction
  $\alpha$: steering effort where 1 is maximum steering curvature and 0 is a straight path
  c: tuning parameter related to width of the distribution about $\theta_d$ The equation above describes the use of a normal, Gaussian distribution to determine the angular velocity, $\hat{\omega}$, of the needle about its primary axis as a function of the difference between current needle angle, $\theta$, and desired direction, $\theta_d$, and is shown representatively in FIG. 2. It should be noted that other distributions or functions may be utilized to replace the Gaussian distribution. A primary contribution of the disclosed approach is underactuated control of the needle such that curvature and direction of the needle insertion path can be controlled based on determining the angular velocity or differential motion as a function of the rotation angle as the needle rotates continuously. Needle rotation velocity is determined as a function of the needle angle as it rotates continuously. The underactuated approach allows control of curvature and direction from a single rotary actuator.

The calculation is performed continuously as the needle rotates to determine the corresponding angular velocity or angle set point.

In one embodiment, needle steering is implemented in software on a control system where the normalized needle rotation angular velocity is calculated in a control loop running at a fixed timer period such as a servo loop running at 1 kHz. The angular velocity of the needle about its primary axis as a function of current angle as it rotates is calculated as:

$$\dot{\theta}(\theta) = \omega_{max}\hat{\omega}$$

Where:
  $\dot{\theta}(\theta)$: needle rotation angular velocity about its primary axis
  $\hat{\omega}$: normalized needle rotation angular velocity about its primary axis
  $\omega_{max}$: maximum angular velocity of needle about its primary axis In one implementation, a discrete time controller is used to determine an angle set point for the next period based on the desired angular velocity as:

$$\theta(t+1) = \theta(t) + \omega_{max}\hat{\omega}T$$

Figure 3:
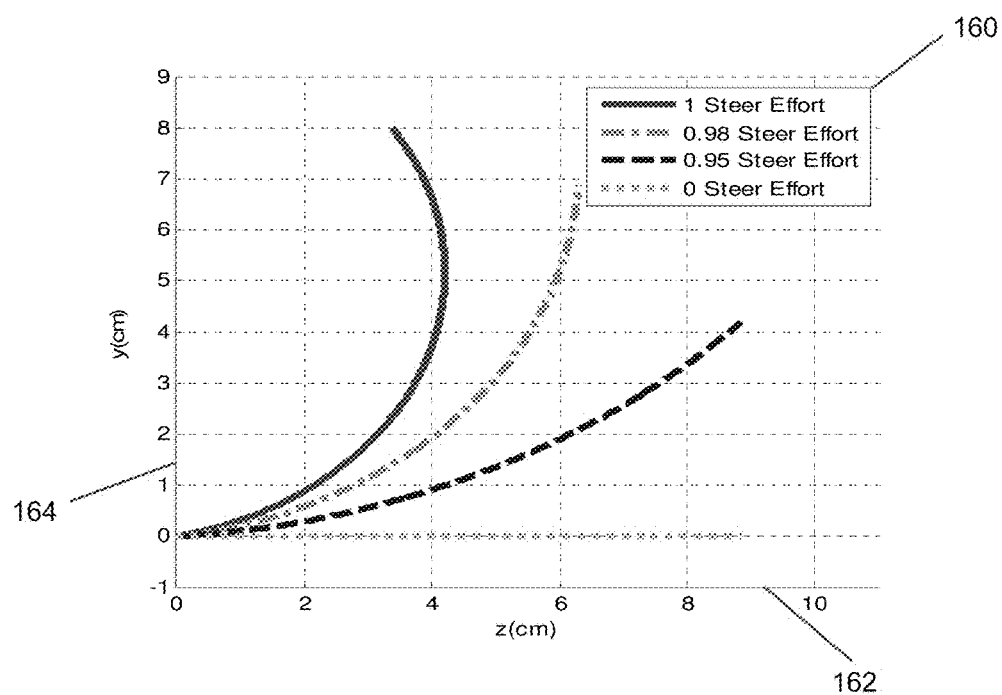
FIG. 3 shows a representation of how needle curvature is affected by changing the steering effort parameter.

Where:
  $\theta(t+1)$: needle rotation angle set point for next period
  $\theta(t)$: needle rotation angle in current period
  $\hat{\omega}$: normalized needle rotation angular velocity about its primary axis
  $\omega_{max}$: maximum angular velocity of needle about its primary axis
  T: time period between cycles of control loop This disclosure refers to the term steering effort which is directly related to curvature, wherein full steering effort corresponds to the maximum curvature and zero steering effort corresponds to a straight insertion with no curvature. In closed loop control, steering effort is used within the control loop to correct a needle insertion path based on a detected error. FIG. 3 shows an exemplary representation of how needle curvature is affected by changing the steering effort parameter, i.e. a representation of how the steering effort, α, relates to the curvature of the needle as it is inserted. Referring to FIG. 3, the overall needle curvature is adjusted by changing this parameter 160. A horizontal axis 162 shows an insertion axis corresponding to the drive (needle) axis 112 (prior to any steering). A vertical axis 164 shows the lateral displacement due to steering, or y-axis. The plot is shown in the plane of the needle's curvature, which may be rotated to any angle about the needle axis, thus enabling control of the needle tip position and the path in 3D. Note that this shows the overall curvature of the needle path, as the tip 144 location during insertion follows a helical profile as the needle rotates during insertion (shown below in FIGS. 6a, 6b, 7 and 8a). The size of the helix may be minimized to provide trajectories that appear as shown. For a fixed steering effort, typically the needle will follow a constant curvature path when all other parameters are constant. The relationship between steering effort and curvature depends on properties of the needle 110, tissue 150, external forces and control parameters.

The specific curvature for a given steering effort is also related to needle properties, tissue properties, and external forces. The steering effort may be run open loop to drive the needle along a specific path, it may be controlled in a closed loop to follow a specific path, or it may be used as a control input to steer the needle towards the target, much like a steering wheel on a car.

Figure 4A:
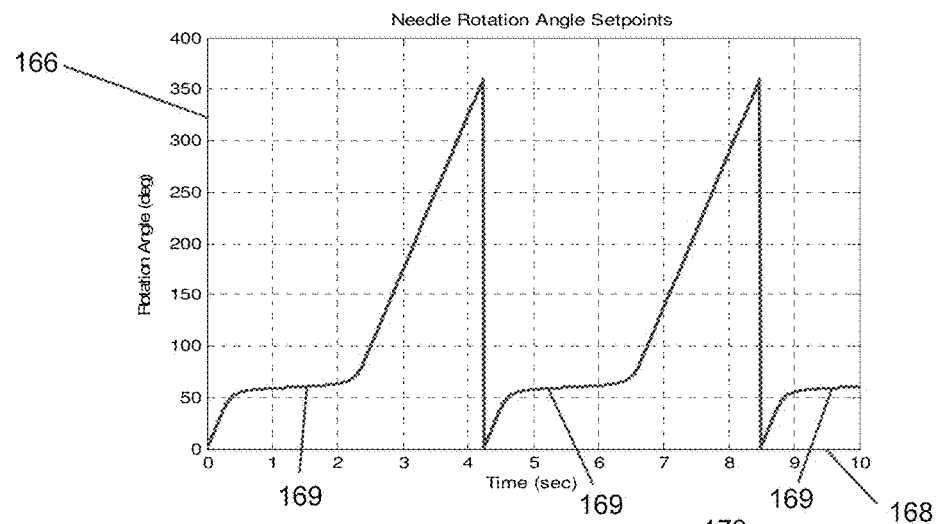
FIGS. 4a and 4b show plots of needle rotation during a controlled insertion
Figure 4B:
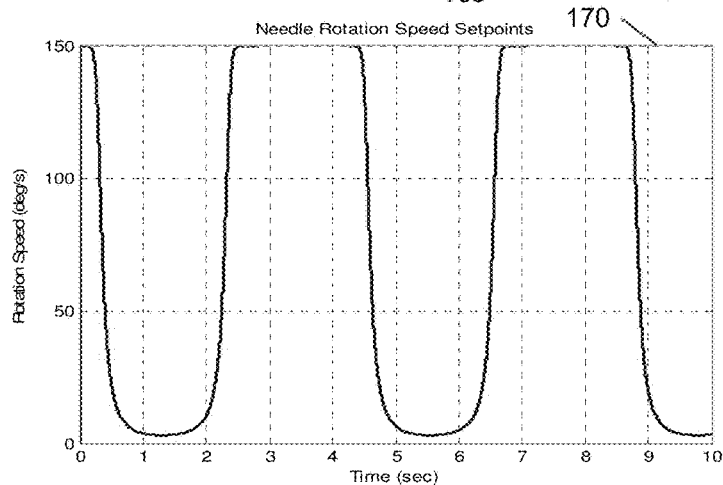

FIGS. 4a and 4b show plots of needle rotation during a controlled insertion. Referring to FIG. 4a, an example of the needle rotation angle about its axis as it spins continuously is show, plotting needle 110 angle as a function of time. The vertical axis 166 shows the rotation cycle (0-360 degrees), and the horizontal axis 168 shows time for each rotation. The region where the angle θ remains closest to horizontal 169 is centered around $θ_d$ with a width related to the tuning parameter c and the steering effort α. FIG. 4b shows the corresponding angular velocity (derivative of the plot in FIG. 4a, also referred to as rotation speed), showing needle 110 angular velocity as a function of time. Note that the angular velocity changes as the needle rotates continuously, where the speed is slower centered on the desired steering direction. The shown pattern repeats with a period related to the set maximum needle rotation angular velocity. The constant velocity segments are at the defined value for $ω_{max}$ at 170. Note that FIGS. 4a and 4b correspond to a representative simulation and that varying control parameters or the specific relationship between angular velocity and angle will vary the shape of the curves. However, the key features are the reduced velocity corresponding to being at or near the desired steering direction.

Figure 5A:
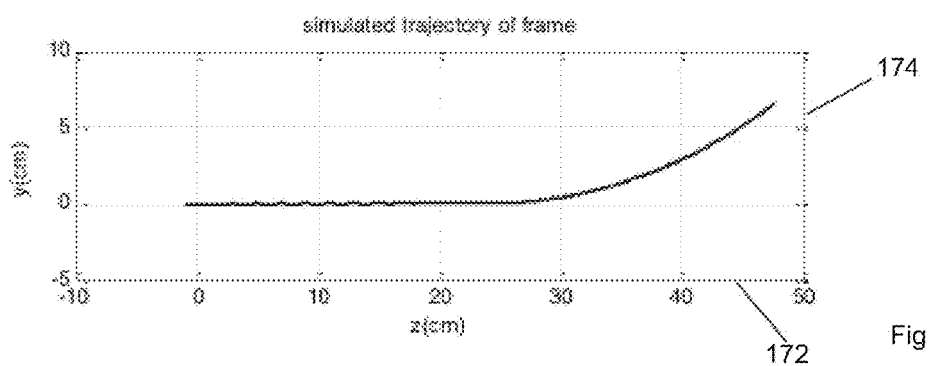
FIGS. 5a-5c show exemplary plot of needle insertion path during a controlled insertion where needle is inserted straight and then at constant curvature.
Figure 5B:
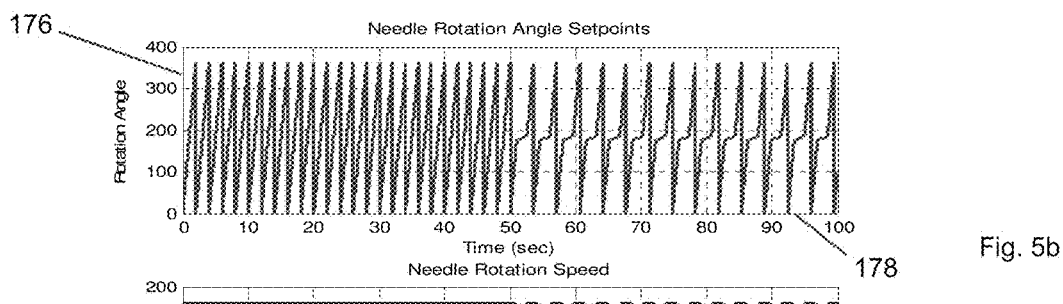
Figure 5C:
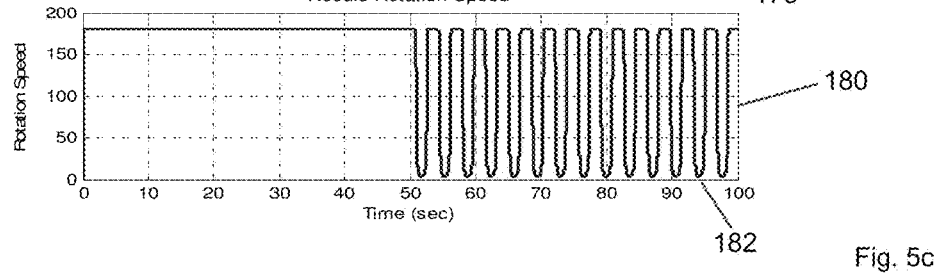

FIGS. 5a-c show exemplary plots of needle insertion path during a controlled insertion where needle is inserted straight and then at a constant curvature. Note that the angular velocity is constant during straight insertion (i.e. drilling during insertion), and varies as previously described during the constant curvature segment. In FIG. 5a, the X-axis 172 (horizontal) represents the displacement along the initial insertion direction and y 174 corresponds to the displacement in steering direction for this example. FIG. 5b is a corresponding plot showing needle angle 176 with respect to time 178. FIG. 5c is a corresponding plot showing needle angular velocity 180 with respect to time 182. Note that the angular velocity 180 is constant during straight insertion (i.e. drilling during insertion), and varies as previously described during the constant curvature segment. Multiple constant curvature segments may be cascaded together, shown further below in FIG. 14.

Figure 6A:
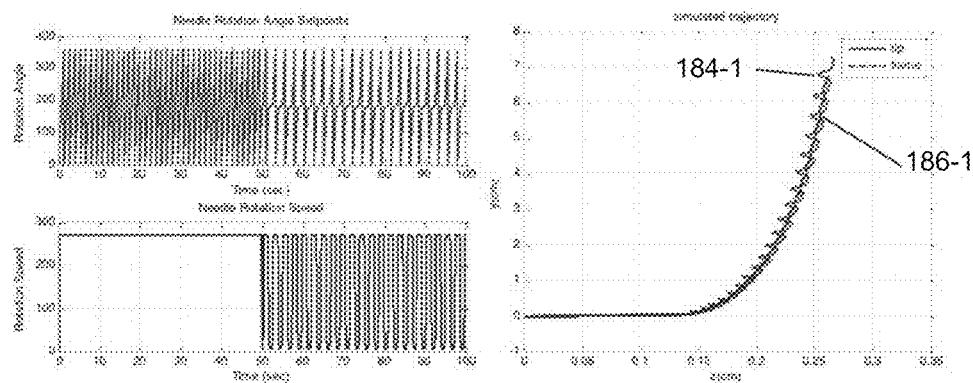
FIGS. 6a-c demonstrate an example where the same overall needle path is achieved with two different configurations.
Figure 6B:
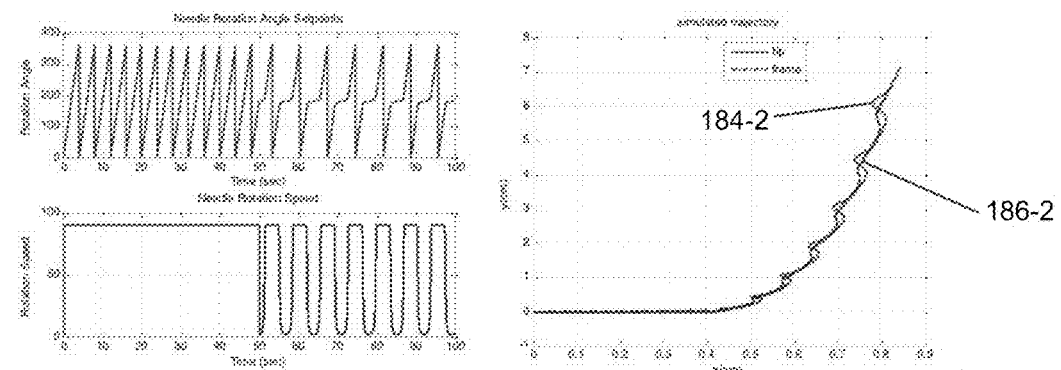
Figure 6C:
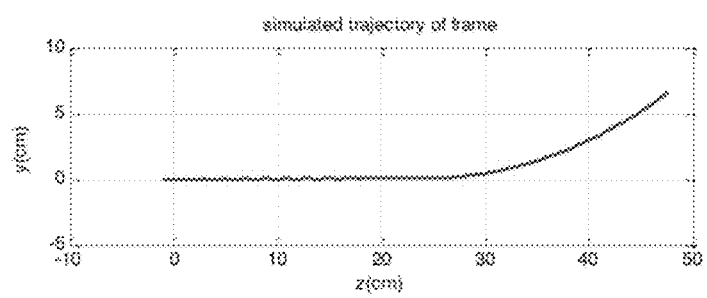

FIGS. 6a-c demonstrate an example where the same overall needle path is achieved with two different configurations, demonstrating needle insertion where the needle goes straight (with constant angular velocity needle rotation) for 50 seconds and then constant curvature (using proposed approach) for 50 seconds. FIG. 6a shows a small diameter helix of tip 144 position during insertion is formed when rotation speed is high relative to insertion speed. FIG. 6b shows a larger diameter helix formed when rotation speed is low relative to insertion. FIG. 6c depicts that the overall needle path (i.e. the path following the center of the helix) is the same for both cases.

In FIGS. 6a and 6b, plot lines 186-1, 186-2 show the shape of the body of the needle after insertion and the corresponding needle angular position and velocity. Plot lines 184-1, 184-2 show the 3D view including the helix that the tip 144 follows as the needle is inserted. The shown helix is exaggerated and can be made negligible with appropriate configuration. Even in the case of straight insertion with constant angular velocity rotation (i.e. drilling), an asymmetric tip needle may follow a helical pitch during insertion.

The insertion is decoupled from the insertion speed, this the overall needle shape at the end of insertion is essentially the same independent of insertion speed. The size of the helical path around that needle shape varies as a function of the relative insertion and rotation speed. For a high rotation speed or low insertion speed, the needle tip path essentially matches the final needle shape after insertion (i.e. negligible helical tip motion).

Figure 7:
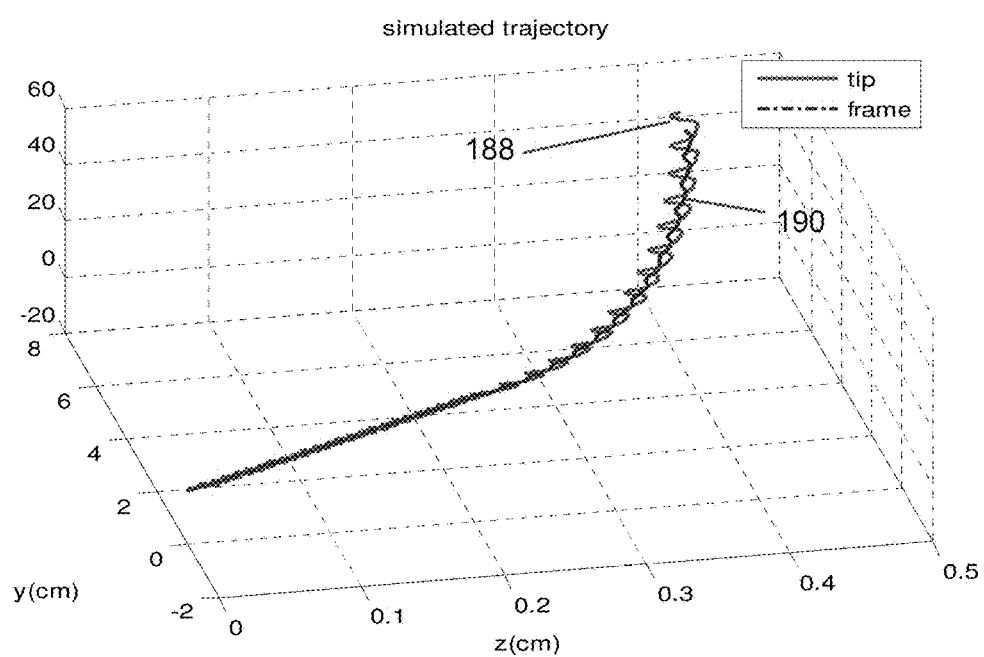
FIG. 7 shows a view of the needle path in 3D for the case of straight, then curved insertion.

FIG. 7 shows a view of the needle path in 3D for the case of straight, then curved insertion. The example 3D view shows tip 188 and frame 190 plots of a controlled needle insertion where the needle goes straight, and then continues with constant curvature. Note that the needle tip 144 moves in a helical pattern (exaggerated in this figure), where the size of the helix is a function of the needle and interaction parameters as well as the relative insertion speed to rotation speed. The frame 146 represents a point set back from the tip on the needle and represents the needle path. This is a representative case of where a needle is driven straight towards an intended target, and then needs to be compensated in order to account for target motion or other errors introduced during the procedure. The figure shows both the exaggerated tip position as it is inserted and the frame position which is set back from the tip which better represents the final needle shape after insertion.

Figure 8A:
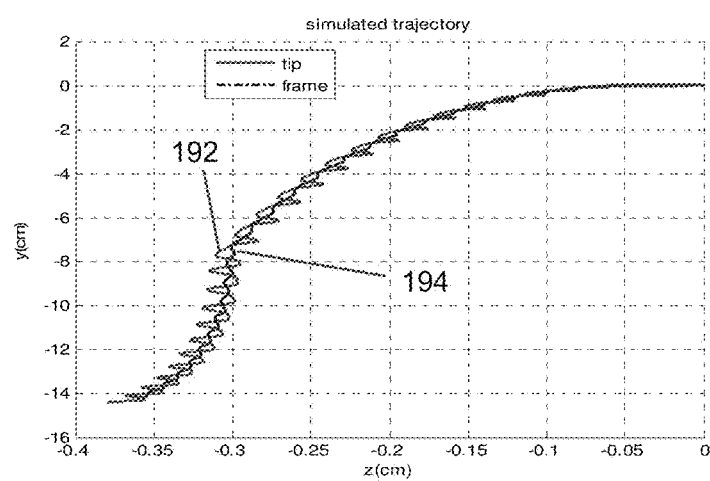
FIGS. 8a-8c show a controlled insertion path where the steering direction changes during the course of insertion.
Figure 8B:
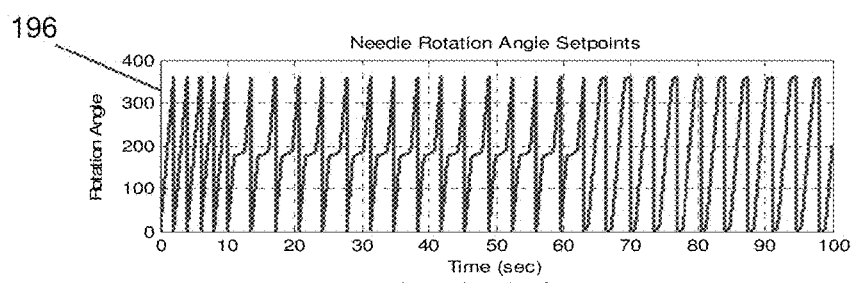
Figure 8C:
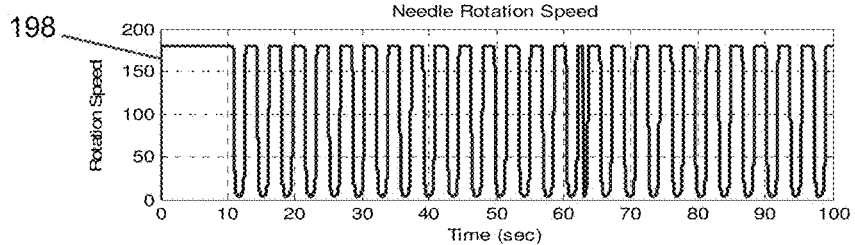

FIGS. 8a-8c shows a representative controlled insertion path where the steering direction changes during the course of insertion. Referring to FIG. 8, the needle 110 inserts straight, then at constant curvature in one direction, and then changes to a different constant curvature in a different direction. Therefore, FIG. 8a depicts an example where the needle 110, tip 192 and frame 194 paths are controlled according to the present configuration along one constant curvature path after a short straight insertion, and then the steering direction and steering effort change to another constant curvature path in a different plane, in response to varied rotation angle 196 and rotation speed 198. Many such paths may be combined together to generate complex 3D trajectories or to continuously compensate for 3D positioning error during insertion. Note how the angular position and velocity plots show distinct differences in the three sections of the needle insertion trajectory.

Figure 9:
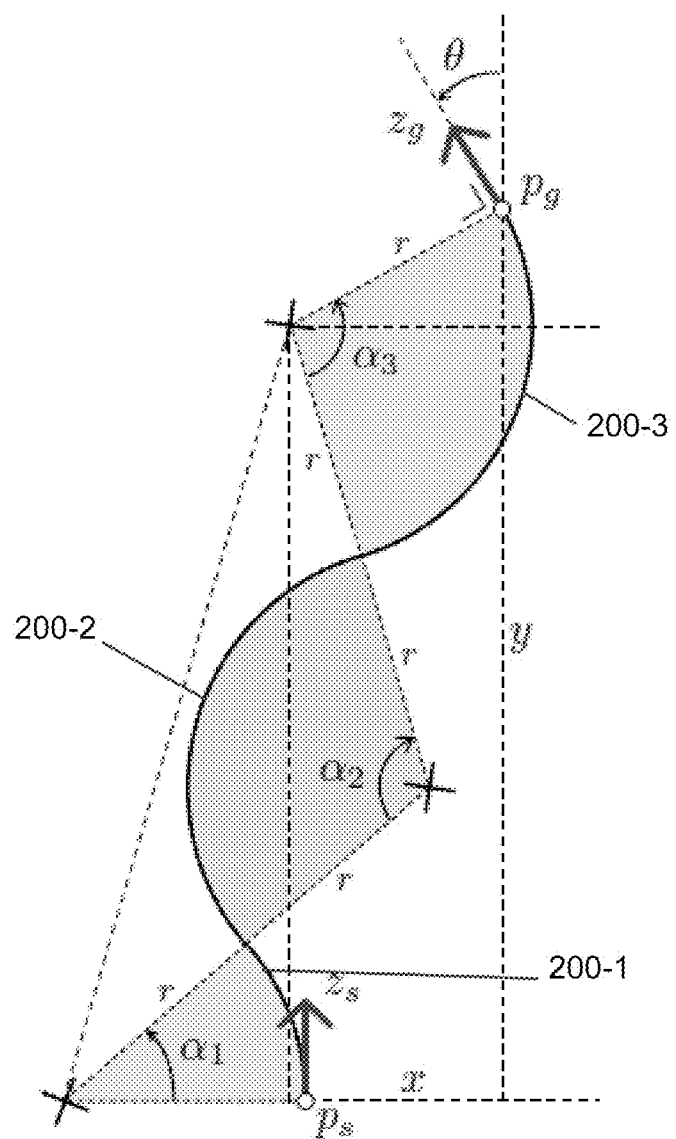
FIG. 9 depicts complex trajectories by combining segments of constant curvature.

FIG. 9 depicts how the proposed approach allows for complex trajectories by combining segments of constant curvature. Referring to FIG. 9, The proposed approach allows for complex trajectories by combining segments 200-1 . . . 200-3 (200 generally) of constant curvature. FIG. 9 demonstrates one example of three segments 200, each with a given curvature (set by steering effort) and a given steering direction (not necessarily in the same plane as shown). Accordingly, FIG. 9 demonstrates one example of three segments, each with a given curvature (set by steering effort) and a given steering direction (not necessarily in the same plane as shown). Large numbers of constant curvature segments may be combined to provide arbitrary paths. The paths of the segments 200 may be precomputed and run open loop, or may be computed on the fly based on closed loop feedback. The shape of the needle 110 during insertion may be determined from any suitable approach including, but not limited to, medical imaging including projection and tomographic images, and strain sensors along the needle including fiber bragg grating (FBG) or fabry-perot interferometry (FPI) sensor. Models may be used to estimate shape based on sparse information such as a small number of cross-sectional images rather than requiring a full 3D representation.

Figure 10:
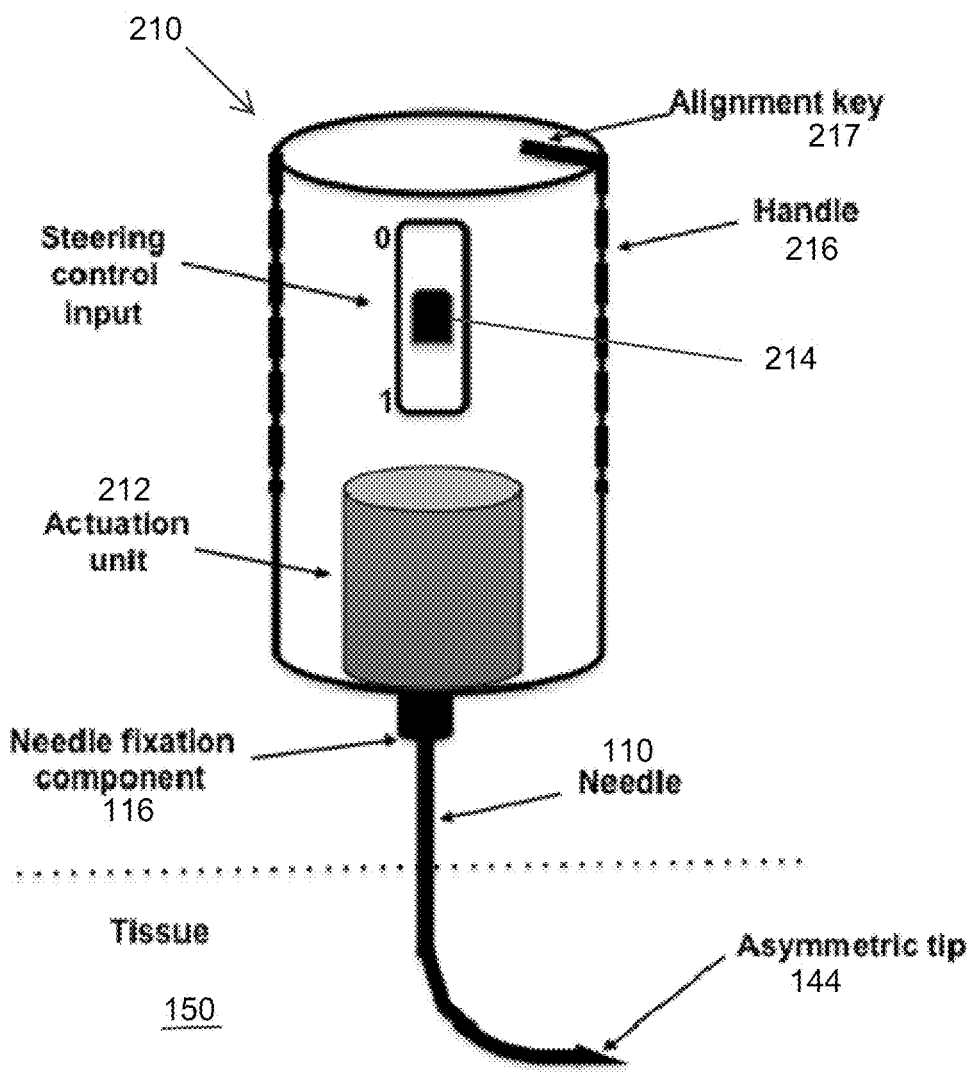
FIG. 10 depicts one embodiment wherein needle curvature during insertion is controlled by a stand-alone device for implementing the needle steering control.

FIG. 10 depicts one embodiment wherein needle curvature during insertion is controlled by a stand-alone device for implementing the needle steering control approach described in the disclosed configuration. In the approach of FIG. 10, needle curvature during insertion is controlled by a stand-alone device that controls steering effort by controlling rotation speed as a function of rotation angle as described in the disclosed configuration. In one embodiment, the device is a handheld device with an integrated actuation unit and steering effort may be controlled by the user. The stand-alone device 210 controls steering effort, thus curvature, by controlling rotation speed as a function of rotation angle as described above. In one embodiment, the device 210 is a handheld device with an integrated actuation unit 212. Steering effort may be fixed or controlled using a switch 214 or other user input. The actuation unit 212 provides rotation of the needle 110. In a further embodiment it also includes needle insertion that can be used for controlling the depth, stabilizing the insertion speed, inserting at high speed, or modulating the insertion. The device 210 may have an integrated needle, or it may have a needle fixation component such as a hub 116 or collet to attach the needle 110. In one embodiment the direction is fixed relative to a handle 216 and marked with an alignment key 217, such that direction is controlled by the user and the device automatically controls curvature. In a further embodiment there is an additional input from user or external source to control the direction relative to the handle. The device 210 may be tracked externally and incorporate semi-autonomous shared control. It should be noted that the device 210 is responsive to manual insertion force provided by an operator, i.e. direct hand pressure.

In one configuration, the handheld device contains a motor, angular position sensor, steering effort control switch, processor, and battery. The device may be fully self contained and steers the needle with a curvature related to the steering effort input. The user may use this with independently obtained interactively updated or real-time imaging. The device may also incorporate a biopsy sample retrieval mechanism. An embodiment of the device may be single use or limited lifetime. This configuration may be used for percutaneous procedures or other access to internal tissues. It may also be used for accessing structures close to the surface such as cannulation of blood vessels, acupuncture, or other medical procedures. In one embodiment, the device is fully compatible with the MRI environment and may be used during MR imaging without significantly degrading image quality.

Figure 11:
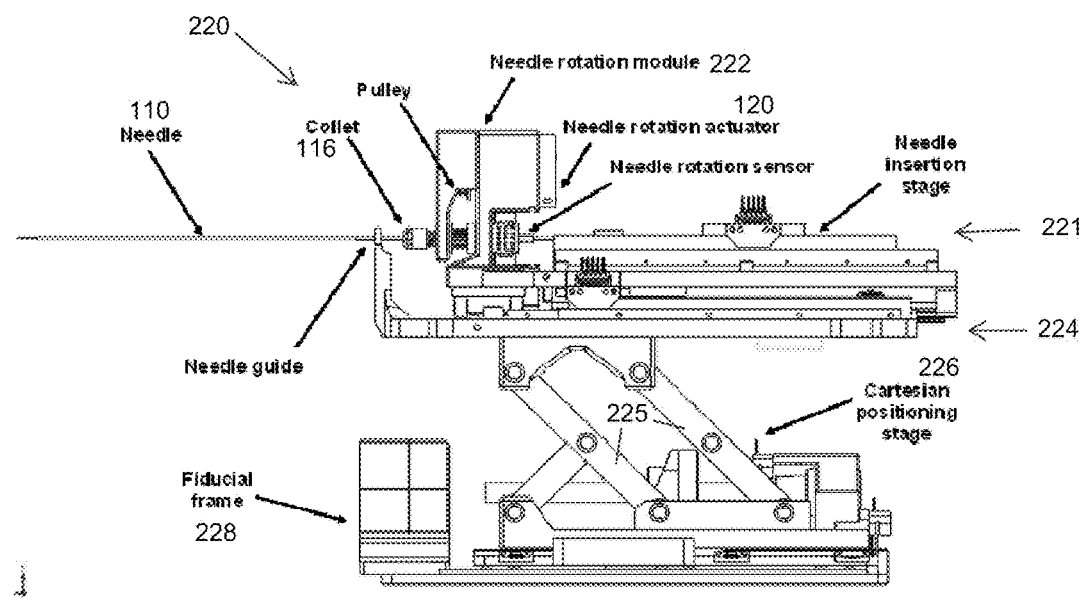
FIG. 11 depicts a particular configuration employing a robot having a needle rotation module.

FIG. 11 depicts a particular configuration of a robotic device 220 to implement the proposed approach for percutaneous interventions. The robot 220 has a needle rotation module 222 packaged in a robotic needle driver module 221 that controls needle angle and holds the asymmetric tip needle 110, which may be a cannulated 113 needle. Needle rotation module 222 is coupled to control logic 122 that may be integrated into module 221 or incorporated into an external device. The needle rotation module 222 resides on a needle insertion module 224, such as an inserter 130, that may have decoupled control from the needle rotation during controlled needle insertion. In one embodiment, a Cartesian stage 226 positions the needle entry point for horizontal translation and vertical orientation via gantry style supports 225, and a fiducial frame 228 is used to localize the robot with respect to the patient or plan. In one embodiment, the fiducial frame 228 employs a z-shaped fiducial pattern to enable localization of the robot and registration to a medical imaging system (e.g. registered to an MRI scanner's patient coordinate frame). Additional methods of actuated or manual positioning may also be utilized.

Figure 12:
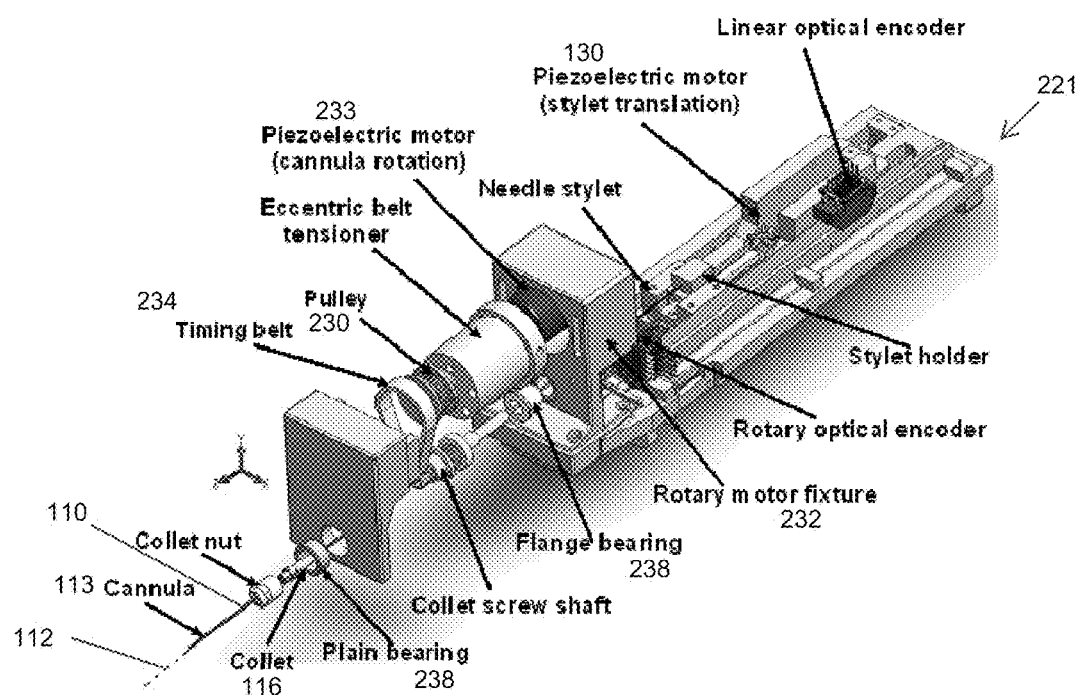
FIG. 12 depicts a configuration of the robotic needle driver module 221 that can be used with the robot device of FIG. 11.

FIG. 12 depicts one embodiment of the robotic needle driver module 221 that can be used with the robot device 220 in depicted in FIG. 11, another robot, or independently. As above, a module or drive 120 controls needle rotation, in this example a piezoelectric motor is used. A further actuator may be used to control a stylet inside of the cannula of a concentric needle. This example shows a standard needle coupled to the robot using a collet.

In this embodiment, a collect 116 holds the asymmetric needle 110 and enables control of rotation about the needle axis 112 and insertion translation. The drive 120 includes a rotary motor 232 for providing the drive 120. A piezoelectric motor 233 or other suitable drive provides a separate rotation source for a cannula 113, augmented by one or more pulleys 230 and belts 234 for controlling rotation of the cannula 113 and/or needle 110 inserted therethrough, as is known with surgical cannulas. The drive 120 may be further facilitated by an eccentric belt tensioner 236, bearings 238, and a linear optical encoder 240 for measuring translation 130 feedback of needle insertion, and a rotary optical encoder 242 for needle rotation angle feedback.

Figure 13:
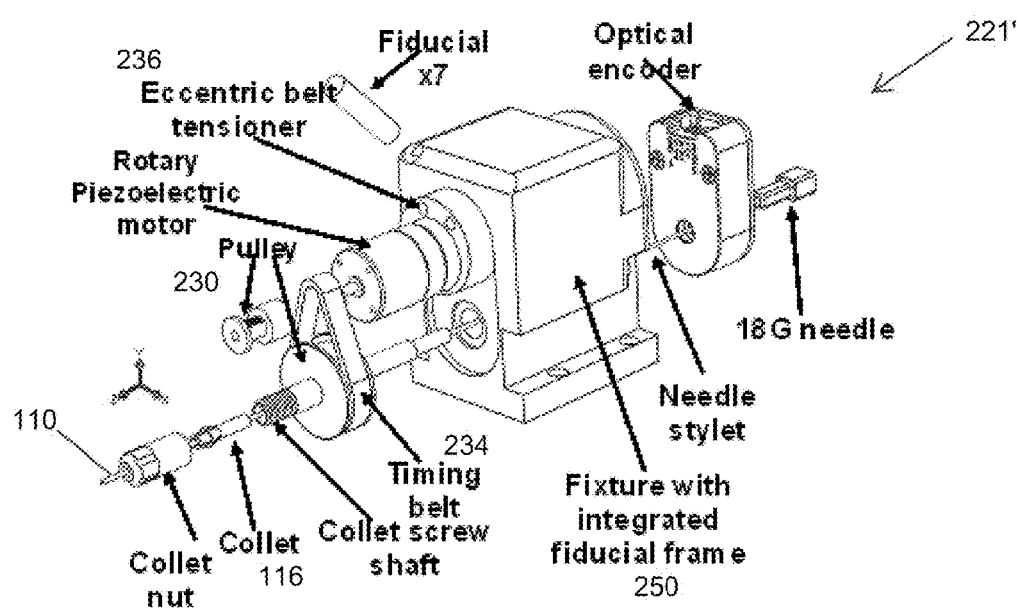
FIG. 13 shows a driver module that can hold standard needles.

A further embodiment of a needle driver is depicted in FIG. 13, employing a driver module 221' that can hold standard needles. The drive module 250 further includes a fiducial frame for localization. The needle driver 221' may be tracked with respect the patient, surgical plan, and/or medical imaging system. In one configuration, imaging fiducials are incorporated into the robotic needle driver. As shown in FIG. 11, z-shaped fiducial frame 225 is incorporated into the robot base or needle driver to localize the system with respect to the medical imaging system. In one configuration, the system is fully compatible with an MRI (Magnetic Resonance Imaging) environment to enable image-guided control of the insertion path based on intra-operative MR images.

Figure 14:
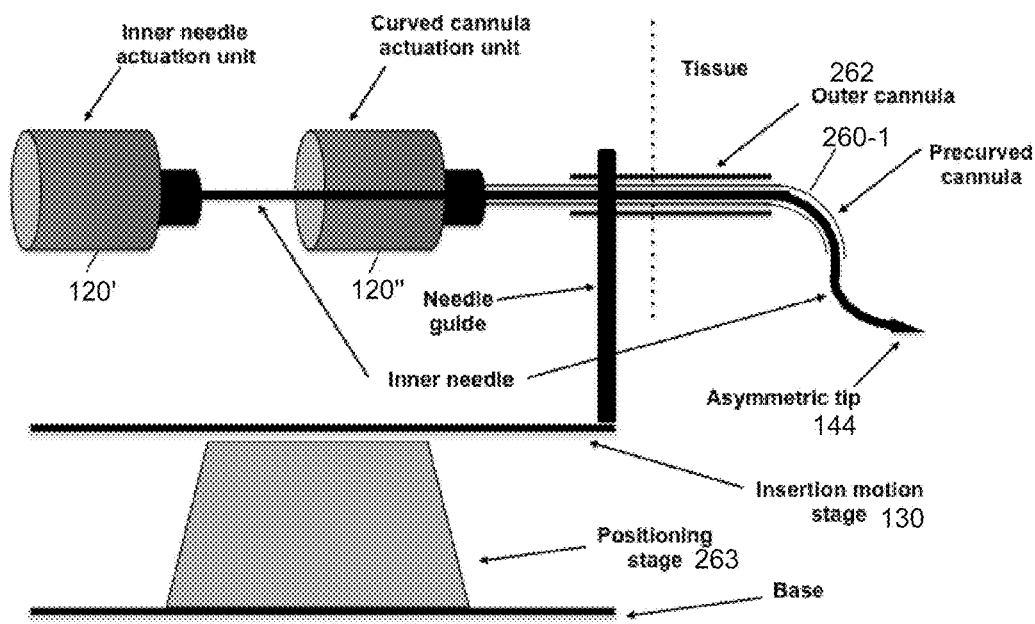
FIG. 14 depicts one embodiment of the system where an asymmetric tip needle is concentric with one or more additional cannulas.

FIG. 14 depicts one embodiment of the system where an asymmetric tip needle 110 is concentric with one or more additional cannulas 260-1 . . . 260-N (260 generally) or tubes, adapted to interface in a telescoping manner or other suitable arrangement. In one configuration, at least one of the concentric cannulas 260 is made of a shape memory material and is precurved. In the configuration shown in FIG. 14, one rigid outer cannula 262 that is positioned in the tissue, one precurved nitinol tube that is manipulated inside the outer cannula 262 using a curved cannula actuation unit 120'. A further solid or hollow needle or cannula 110' with an asymmetric tip is manipulated inside of the precurved cannula 260 using the inner needle actuation unit. The actuation units 120', 120" provide insertion and rotation of the corresponding needle in this embodiment. Note that this represents an exemplary case and that multiple straight, precurved or prebent, and asymmetric tip needle 144, cannulas, tubes, rods, and other instruments may be cascaded together. The asymmetric needle 144 may be controlled using the approach described in the disclosed configuration. This control may be used after initial positioning via positioning stage 263 of the concentric delivery tubes 260, or may be used to provide additional control of the needle insertion path 152 as the concentric cannulas 260 are inserted.

Figure 15:
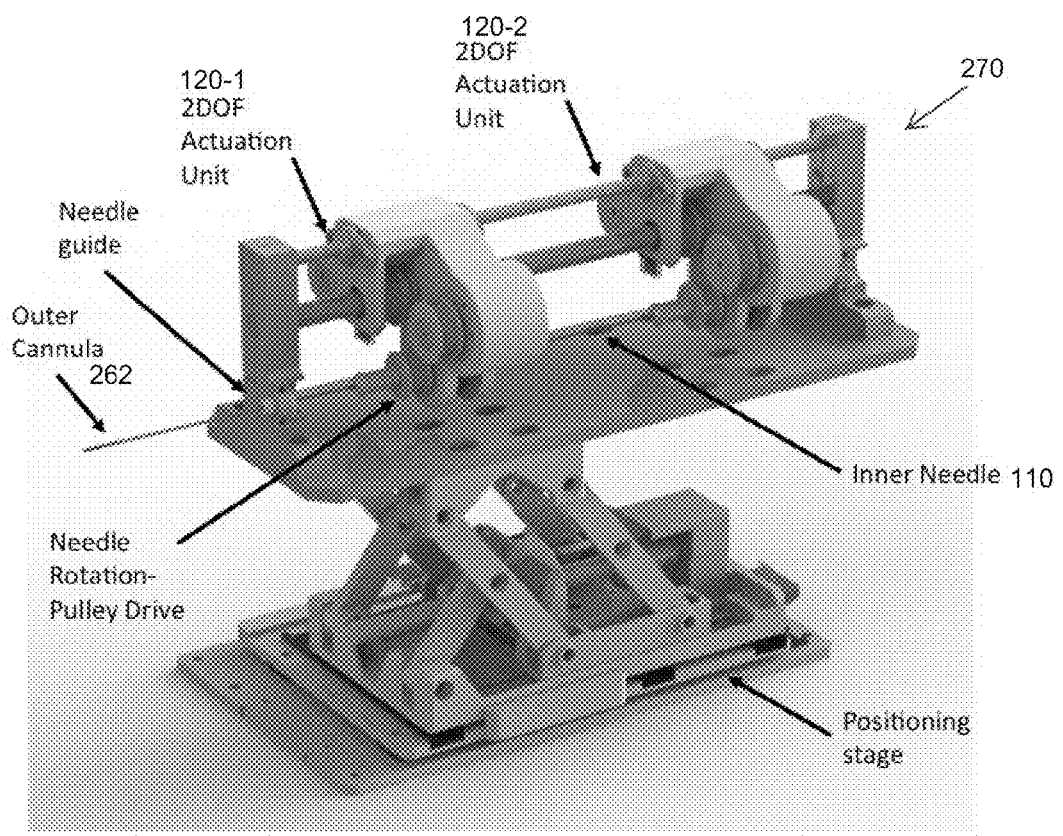
FIG. 15 depicts one exemplary embodiment of a robotic needle driver capable of manipulating both a precurved cannula.

FIG. 15 depicts one exemplary embodiment of a robotic needle driver capable of manipulating both a precurved cannula 260 and an asymmetric tip needle 144. This apparatus 270 can be controlled using the approach discussed above. The asymmetric tip 144 may be used to control the insertion of the inner needle after being positioned, or to manipulate the path 152 during insertion of the precurved cannula component 260. In one configuration, the inner needle 110 may be a hollow core needle or cannula. The asymmetric tip may be on the inner stylet, the outer cannula of the needle, or both. The modular, reconfigurable needle driver is composed of 2 or more motor actuation units 120-1, 120-2 each capable of 2 degrees of freedom (rotation and translation of the needle or tube) capable of controlling two needle components (cannulated and inserted through the cannulated bore 110'). In one configuration, the outer cannula is precurved and the inner needle has an asymmetric tip 144 that is steered as described above. Multiple tubes (cannulas 260) may be cascaded together with multiple actuation units 120-N.

Figure 16:
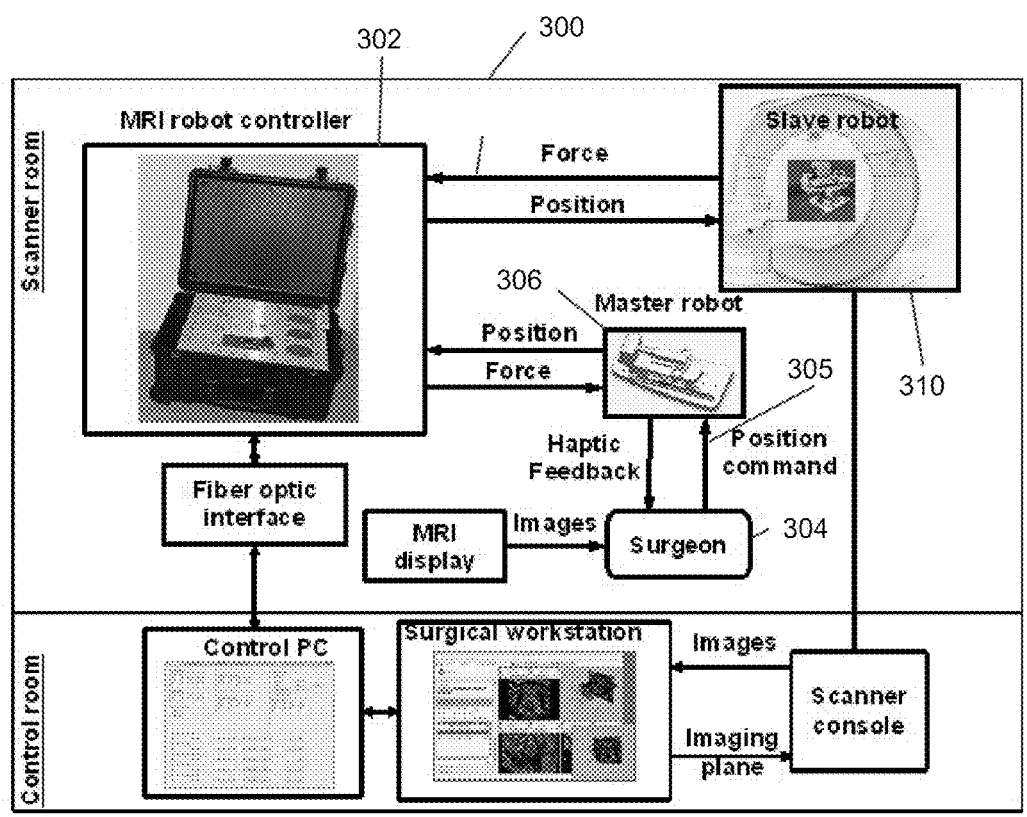
FIG. 16 shows a representative teleoperation framework.

FIG. 16 shows a representative teleoperation framework 300 that enables semi-autonomous shared control of needle insertion. Semi-autonomous shared control refers to the system determining a degree of compensation to be provided, and that adjustment in the needle path 152 is made automatically using the disclosed approach while the user only directly controls the insertion depth. In an example MRI environment, a surgeon 304 manipulates a user control 306, such as a teleoperation interface, haptic device, joystick, slide, knob, or any suitable control, for providing a positioning command 305 pertaining to insertion to a robotic controller 302 via a master robot or other user control 306. The master robot or user control device 306 relays the command including position information to a slave robot 310 and in turn, to the needle insertion actuator or inserter 130. Feedback force may be provided, which may take the form of haptic feedback such as resistance of vibration, to indicate drilling conditions to the surgeon 304, such as bone or dense tissue. Feedback force may be measured by force sensors integrated into slave robot 310 and reflected back to the user through actuators in master robot 306. This may be performed under live image guidance with medical imaging modalities including: ultrasound, x-ray, fluoroscopy, computed tomography (CT), magnetic resonance imaging (MRI), and 2D or 3D video. Guidance may also be performed using an external tracking system or additional information from sensors on the instrument, outside the body, or in the body. One embodiment of the approach is designed to be fully compatible with the MRI environment, wherein the user operates a master robot 306 from beside an MRI scanner bore, while the salve robot is inside the bore of the MRI scanner with the patient.

Figure 17:
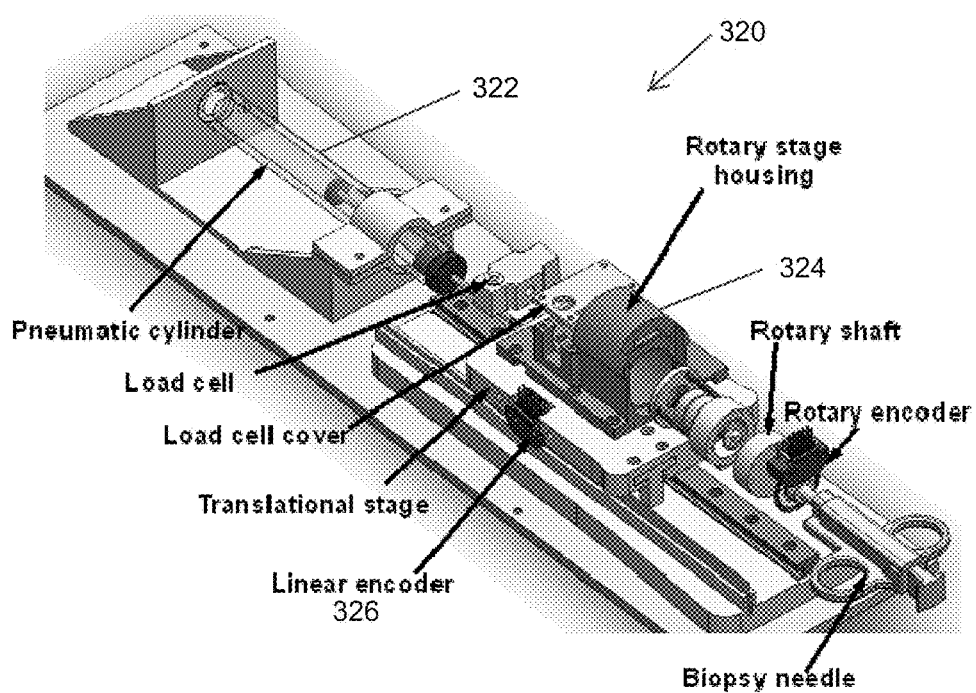
FIG. 17 depicts an example of a teleoperation master.

FIG. 17 depicts an example of a teleoperation master. Referring to FIGS. 1, 16 and 17, the teleoperation master 320 may be used to control the insertion depth of the needle by manipulating the translation stage and linear encoder 326. As with the above configurations, insertion may be controlled independent of the needle rotation during controlled steering. In one embodiment, the teleoperation master 320 provides force feedback to the user, this may be accomplished with pneumatics or other actuation technologies, such as via pneumatic cylinder 322. Force feedback may be open loop or closed loop. The master 320 may include a rotary stage 324 to control either the needle rotation angle directly or the desired steering angle of the proposed control approach. An additional input may be added to control steering effort. In one embodiment, the steering angle and the steering effort are controlled autonomously while the user controls insertion depth using a haptic master, hence receiving feedback of needle 110 steering progress.

Figure 18:
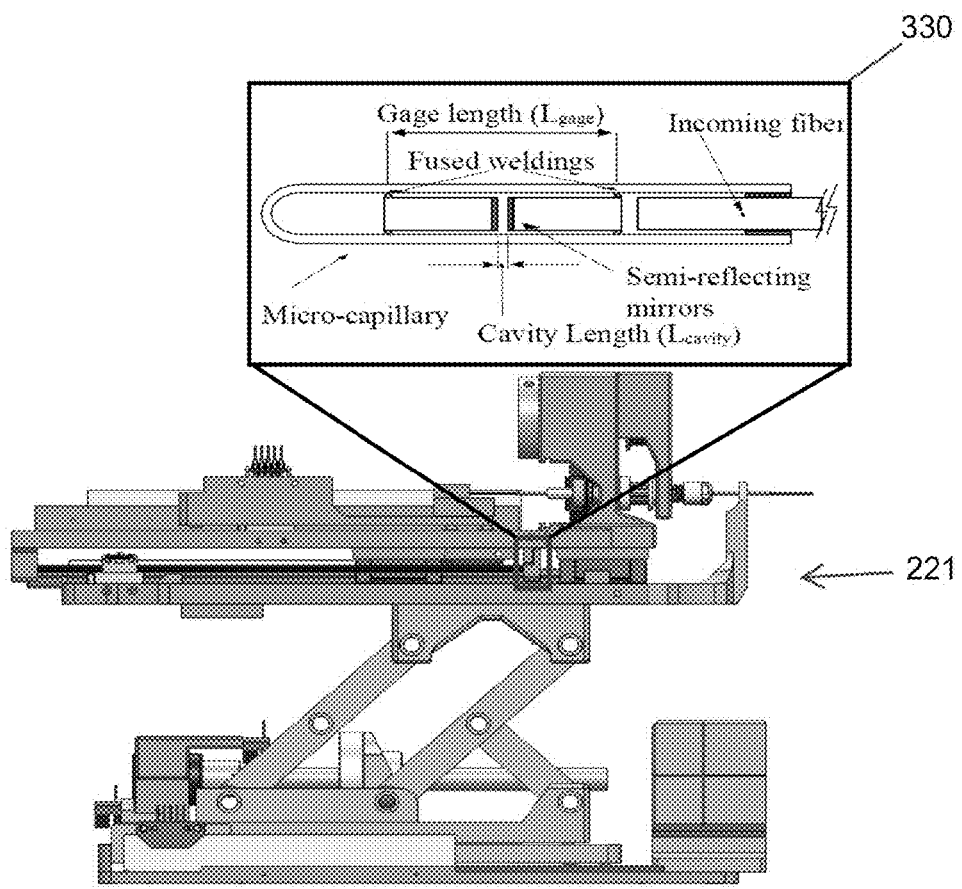
FIG. 18 depicts a needle driver module incorporating a force sensor.

FIG. 18 depicts one embodiment of a needle driver module incorporating a force sensor. Referring to FIGS. 1 and 18, a force sensor 330, disposed on an insertion module 221, may be a fiberoptic sensor such as an FPI, FBG, or light intensity-based sensor, or another sensing technology including but not limited to strain gauges or load cells. Additionally, torque sensors may be used in a needle driver to estimate torsional load on the needle. This information may be used to compensate for difference in angular position or velocity between the base and tip. In one configuration, the forces measured by the force sensor are reflected to the user through a haptic teleoperation master, as in FIG. 16.

In alternate configurations, a slave robot is actuated using piezoelectric motors and incorporates FPI fiberoptic force sensing. The slave robot has a needle rotation module capable of using the proposed steering approach. The master device measures needle translation that controls slave needle insertion depth and optionally rotation that may be used to control steering angle either directly or through the proposed steering approach. In a further configuration, force feedback may be provided on the haptic mater device using pneumatics or other actuation technologies. A configuration of the system uses hybrid actuation with pneumatic control of the master robot and piezoelectric actuation of the slave robot. One embodiment of the system is MRI-compatible to enable the controller, master, and slave to reside inside an MRI scanner room and be used during imaging without significantly degrading image quality.

In another arrangement, the apparatus and methods disclosed above may be integrated into a system configuration for teleoperated control of the needle inside the MRI scanner. In one configuration, the target is tracked in interactively updated MRI images. The user control insertion depth of the needle held by the slave robot using the master robot device. The user can visualize the insertion progress in interactively updated MR images. In one configuration, the needle may be autonomously steered to reach the target, while the user only directly controls insertion depth or insertion speed. In this configuration, the target and needle are tracked in interactively updated medical images, and the control system uses the teachings of the resent invention to steer the needle to the target (i.e. active compensation of the path) while the user (e.g. a clinician) controls the insertion depth or insertion speed using a master device while visualizing the needle insertion. This enables the clinician control over depth, thus potentially improving safety over a fully autonomous system, while enable the control system to ensure the needle reaches the target even in the presence of deformation. In an alternate configuration, the needle driver robot is not actuated along needle insertion (only position sensing along the insertion direction), and the user directly inserts the needle by pushing on the needle driver (without a separate teleoperation master) while the rotation module autonomously steers the needle according to the teachings of the disclosed configuration.

The above description provides detail about exemplary configurations and algorithms of the disclosed configuration's teachings; however, the disclosed configuration is not restricted to only the specific configuration or approaches shown.

The present configurations may be practiced by employing conventional materials, methodology and equipment. Accordingly, the details of such materials, equipment and methodology are not set forth herein in detail. In the previous descriptions, numerous specific details are set forth, such as specific materials, structures, processes, etc., in order to provide a thorough understanding of the disclosed configuration. However, it should be recognized that the disclosed configuration can be practiced without resorting to the details specifically set forth. Only an exemplary embodiment of the disclosed configuration and but a few examples of its versatility are shown and described in the present disclosure. It is to be understood that the disclosed configuration is capable of use in various other combinations and environments and is capable of changes or modifications within the scope of the inventive concept as expressed herein.

Those skilled in the art should readily appreciate that the programs and methods defined herein are deliverable to a user processing and rendering device in many forms, including but not limited to a) information permanently stored on non-writeable storage media such as ROM devices, b) information alterably stored on writeable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), microcontrollers, state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims

The invention claimed is:

1. A needle steering apparatus for steering a needle along a path during insertion, the apparatus comprising:
   a needle having a longitudinal axis and including an asymmetric tip defined by a beveled cut across a cylindrical cross section of the needle, the angle of the beveled cut relative to the longitudinal axis defining a control angle;
   a rotary drive continuously rotating the needle about an axis of rotation coincident with the longitudinal axis of the needle, the rotary drive responsive to control logic adapted to rotate the needle at a time varying angular velocity based on an angular position of the control angle about the axis of rotation of the needle; and
   an inserter for disposing the needle axially in a direction of along the longitudinal axis of the needle, the angular velocity independent from the rate of insertion,
   wherein the direction of insertion and curvature of the needle is controlled during insertion for steering the needle along the path.

2. The apparatus of claim 1, wherein the control logic enables independent control of the rotary driver from that of the inserter.

3. The apparatus of claim 1, wherein the control logic enables underactuated control of both curvature and direction of a needle path from the rotary drive.

4. The apparatus of claim 1 further comprising a teleoperation master device configured for providing control of the inserter.

5. The teleoperation control of claim 4, wherein the teleoperation master device is responsive to physical counterforce on the needle for providing corresponding feedback to a user.

6. The apparatus of claim 1 further comprising one or more additional drives and a cannulated delivery mechanism, the cannulated delivery mechanism configured to define a cannula for at least a portion of a path to a surgical target, the cannula responsive to insertion of the needle for disposing the needle beyond an end of the cannula.

7. The apparatus of claim 1 further comprising a needle driver, the needle driver for controlling the rotary drive and the inserter, the needle driver mechanically coupled to a fiducial frame for locating the needle driver relative to a patient, medical images of a patient, and/or a surgical plan.

8. A method for inserting a needle into tissue along a curved path, the needle inserting method comprising:
   providing a needle having a longitudinal axis and including an asymmetric tip defined by a beveled cut across a cylindrical cross section of the needle, the angle of the beveled cut relative to the longitudinal axis defining a control angle;
   continuously rotating the needle about an axis of rotation coincident with the longitudinal axis of the needle;
   inserting the needle via a control having at least two degrees of freedom, each of the degrees of freedom independent from the other degrees of freedom; and
   one of the degrees of freedom being responsive to an angular position for continuously rotating the needle at a time varying angular velocity, wherein the time varying angular velocity rotation is a function of the angular position of the control angle about the axis of rotation of the needle.

* * * * *